United States Patent
Schulze et al.

[19]

[11] Patent Number: 6,131,789
[45] Date of Patent: *Oct. 17, 2000

[54] SURGICAL STAPLER

[75] Inventors: Dale R. Schulze, Leam; Jon A. Sherman, Cincinnati, both of Ohio

[73] Assignee: Ethicon, Inc., Somerville, N.J.

[ * ] Notice: This patent is subject to a terminal disclaimer.

[21] Appl. No.: 08/232,906

[22] Filed: Apr. 25, 1994

Related U.S. Application Data

[63] Continuation of application No. 08/038,587, Mar. 26, 1993, which is a continuation of application No. 07/855,183, Mar. 20, 1992, Pat. No. 5,275,323, and a continuation of application No. 07/620,119, Nov. 30, 1990, Pat. No. 5,129,570.

[51] Int. Cl.⁷ .................................................. A61B 17/064
[52] U.S. Cl. .................................... 227/175.4; 227/175.2; 227/180.1; 227/19
[58] Field of Search ................................. 227/19, 175.1, 227/175.2, 175.3, 175.4, 176.1, 180.1, 178.1; 606/220

[56] References Cited

U.S. PATENT DOCUMENTS

| | | |
|---|---|---|
| 2,174,219 | 9/1939 | Balma . |
| 2,246,647 | 6/1941 | Vancura . |
| 3,079,606 | 3/1963 | Bobrov et al. . |
| 3,490,675 | 1/1970 | Green et al. . |
| 3,499,591 | 3/1970 | Green . |
| 3,545,444 | 12/1970 | Green . |
| 3,665,924 | 5/1972 | Noiles et al. . |
| 3,675,688 | 7/1972 | Bryan et al. . |
| 3,735,762 | 5/1973 | Bryan et al. . |
| 3,740,994 | 6/1973 | DeCarlo, Jr. . |
| 3,780,416 | 12/1973 | Rider . |
| 3,844,289 | 10/1974 | Noiles . |
| 3,873,016 | 3/1975 | Fishbein . |
| 3,955,581 | 5/1976 | Spasiano et al. . |
| 4,086,926 | 5/1978 | Green et al. . |
| 4,202,480 | 5/1980 | Annett . |
| 4,204,623 | 5/1980 | Green . |
| 4,256,251 | 3/1981 | Moshofsky . |
| 4,354,628 | 10/1982 | Green . |
| 4,372,316 | 2/1983 | Blake, III et al. . |
| 4,391,401 | 7/1983 | Moshofsky . |
| 4,429,695 | 2/1984 | Green . |
| 4,473,077 | 9/1984 | Noiles et al. . |
| 4,500,025 | 2/1985 | Skwor . |
| 4,506,670 | 3/1985 | Crossley . |
| 4,519,532 | 5/1985 | Foslien . |
| 4,520,817 | 6/1985 | Green . |
| 4,523,707 | 6/1985 | Blake, III et al. . |
| 4,527,724 | 7/1985 | Chow et al. . |
| 4,556,058 | 12/1985 | Green . |
| 4,566,620 | 1/1986 | Green et al. . |
| 4,569,346 | 2/1986 | Poirier . |
| 4,576,165 | 3/1986 | Green et al. . |
| 4,576,167 | 3/1986 | Noiles . |
| 4,589,416 | 5/1986 | Green . |
| 4,591,085 | 5/1986 | DiGiovanni . |
| 4,597,517 | 7/1986 | Wagdy . |
| 4,606,343 | 8/1986 | Conta et al. . |
| 4,606,345 | 8/1986 | Dorband et al. . |
| 4,608,981 | 9/1986 | Rothfuss et al. . |
| 4,612,933 | 9/1986 | Brinkerhoff et al. . |
| 4,619,262 | 10/1986 | Taylor . |
| 4,633,861 | 1/1987 | Chow et al. . |
| 4,633,874 | 1/1987 | Chow et al. . |
| 4,646,745 | 3/1987 | Noiles . |
| 4,664,305 | 5/1987 | Blake, III et al. . |
| 4,665,916 | 5/1987 | Green . |
| 4,807,628 | 2/1989 | Peters et al. . |
| 4,809,898 | 3/1989 | Gassner et al. . |
| 4,850,355 | 7/1989 | Brooks et al. . |
| 4,863,088 | 9/1989 | Redmond et al. . |

(List continued on next page.)

*Primary Examiner*—Rinaldi I. Rada
*Assistant Examiner*—Boyer Ashley
*Attorney, Agent, or Firm*—Paul A. Coletti

[57] ABSTRACT

The present invention relates to an improved surgical stapler that prevents refiring of a spent staple cartridge. More specifically, this invention includes a simple, inexpensive mechanical locking mechanism which prevents refiring of a spent staple cartridge by blocking the path of the firing and/or cutting means of the stapler.

19 Claims, 7 Drawing Sheets

U.S. PATENT DOCUMENTS

| | | |
|---|---|---|
| 4,881,544 | 11/1989 | Green et al. . |
| 4,892,244 | 1/1990 | Fox et al. . |
| 4,932,960 | 6/1990 | Green et al. . |
| 4,938,408 | 7/1990 | Bedi et al. . |
| 4,955,959 | 9/1990 | Tompkins et al. . |
| 5,031,814 | 7/1991 | Tompkins et al. . |
| 5,106,008 | 4/1992 | Tompkins et al. . |
| 5,129,570 | 7/1992 | Schulze et al. ............................ 227/19 |
| 5,156,315 | 10/1992 | Green et al. ......................... 227/178.1 |
| 5,275,323 | 1/1994 | Schulze et al. ...................... 227/176.1 |
| 5,673,842 | 10/1997 | Bittner et al. ........................ 227/175.4 |
| 5,878,938 | 3/1999 | Bittner et al. ........................ 227/175.4 |

SURGICAL STAPLER

This is a continuation of application Ser. No. 08/038,587, filed Mar. 26, 1993, still pending, which is a continuation of application Ser. No. 07/855,183, filed Mar. 20, 1992, now U.S. Pat. No. 5,275,323, which is a continuation of application Ser. No. 07/620,119, filed Nov. 30, 1990, now U.S. Pat. No. 5,129,570.

BACKGROUND OF THE INVENTION

1. Field of the Invention

The present invention relates to an improved surgical stapler that prevents refiring of a spent staple cartridge. More specifically, this invention includes an inexpensive, simple and reliable mechanical locking mechanism that prevents refiring of a spent staple cartridge.

2. Description of the Related Art

Before surgical staplers were introduced surgeons had to spend a great deal of time sewing the tissue of patients back together. This was the most time intensive aspect of a surgical procedure. Surgical staplers have decreased the amount of time that a user spends sewing tissue back together.

Another concern is whether the staplers used during procedures are sterile. Reusable staplers, being a relatively complicated mechanical instrument, are difficult to sterilize after use. Hence, it is desired that the surgical stapler be disposable. As more than one surgical stapler may be required in a surgical procedure, for economical reasons disposable surgical staplers having reloadable staple cartridges have been developed.

It is desired that operating room personnel be able to quickly reload a disposable surgical stapler with an unspent staple cartridge during a surgical procedure. This is significant because as the amount of time it takes to reload a stapler is decreased, the amount of time that the whole procedure takes is also decreased. This means the amount of risk to the patient is less during a procedure of shorter duration. For example, the patient will not have to be under anesthesia as long during a shorter procedure. However, delay occurs when a used cartridge is inadvertently reloaded in the stapler or a used cartridge is not removed before an attempt is made to use the stapler.

There are various types of staplers. Some staplers perform the sole function of stapling while other types of staplers also perform additional functions. For example, one type of surgical stapler has parallel rows of staples with a slot for a cutting means to travel between the rows of staples. This type of surgical stapler minimizes bleeding by applying the outside rows of staples to layers of surrounding tissue as the cutting means pierces through the tissue in between the staples. In such a stapler, if it is not recognized that a spent cartridge is in the stapler the user may attempt to cut tissue without the staples being inserted alongside the incision made by the knife.

As a result of the concern about such occurrences there have been attempts made in the art to provide such disposable surgical staplers with locking mechanisms that reduce possible delays or potential harm to a patient. Unfortunately, the locking mechanisms of these staplers are not inexpensive, simple, or necessarily reliable.

For example, Green, U.S. Pat. No. 4,086,926 (hereinafter "Green") describes a stapler that has a cartridge that contains a means for locking itself during shipment and preventing the inadvertent severing of organic structures when all of the staples, for example, have been expelled from the cartridge. Green describes a complex staple cartridge locking system that is embodied in the cartridge. The Green cartridge includes the following; a rail assembly, an anvil means, an elongate main body, a pair of belts mounted in the elongate main body, a plurality of surgical staples carried by the above-mentioned belts, a pair of pushers, ramp means, a knife, and shifter means associated with the knife. Since the cartridge has all these elements in it it is complex and relatively expensive to manufacture.

SUMMARY OF THE INVENTION

In accordance with the present invention a surgical stapler is provided for applying a plurality of rows of staples housed in a disposable cartridge. The cartridge has a slot disposed between adjacent rows of staples that extends substantially the entire length of the rows of staples. The stapler includes firing means for the staples and a cutting means movable in the slot. The cutting means has a bottom surface, a top surface, and a cutting edge. The stapler also includes a locking mechanism for preventing movement of the cutting means in the slot. The locking mechanism comprises a leaf spring disposed in the stapler that engages the bottom surface of the cutting means to place the cutting means in a first position. In the first position the cutting means is out of alignment with the slot. Also, there are means disposed on the cartridge for engaging the top surface of the cutting means. The means for engaging the top surface of the cutting means depresses the leaf spring and moves the cutting means from the first position to a second position. In the second position the cutting means is in alignment with the slot so the cutting means may move within the slot.

In one embodiment of the surgical stapler the means disposed on the cartridge for engaging the top surface of the cutting means is a rotatable member which moves the cutting means from a first position to a second position.

In another embodiment of the surgical stapler the means disposed on the cartridge for engaging the top surface of the cutting means is a configured wire member that begins near the front of the cartridge slot and is disposed along substantially the entire length of the cartridge slot to the rear of the staple cartridge. This embodiment includes cavities molded in the staple cartridge which cooperate with the wire member to move the cutting means from a first position to a second position.

In yet another embodiment of the surgical stapler the means disposed on the cartridge for engaging the top surface of the cutting means is a breakable member. The member is broken upon moving the cutting means from the first position to the second position.

The preferred embodiments of the surgical staplers of the present invention have two adjacent rows of staples on each side of the cartridge slot. Also, in the preferred embodiments the cutting means is a knife blade assembly.

DETAILED DESCRIPTION OF SPECIFIC EMBODIMENTS

Reference will now be made in detail to specific embodiments of the present invention which are conveniently described by reference to the accompanying FIGS. 1–13.

Figure 1:
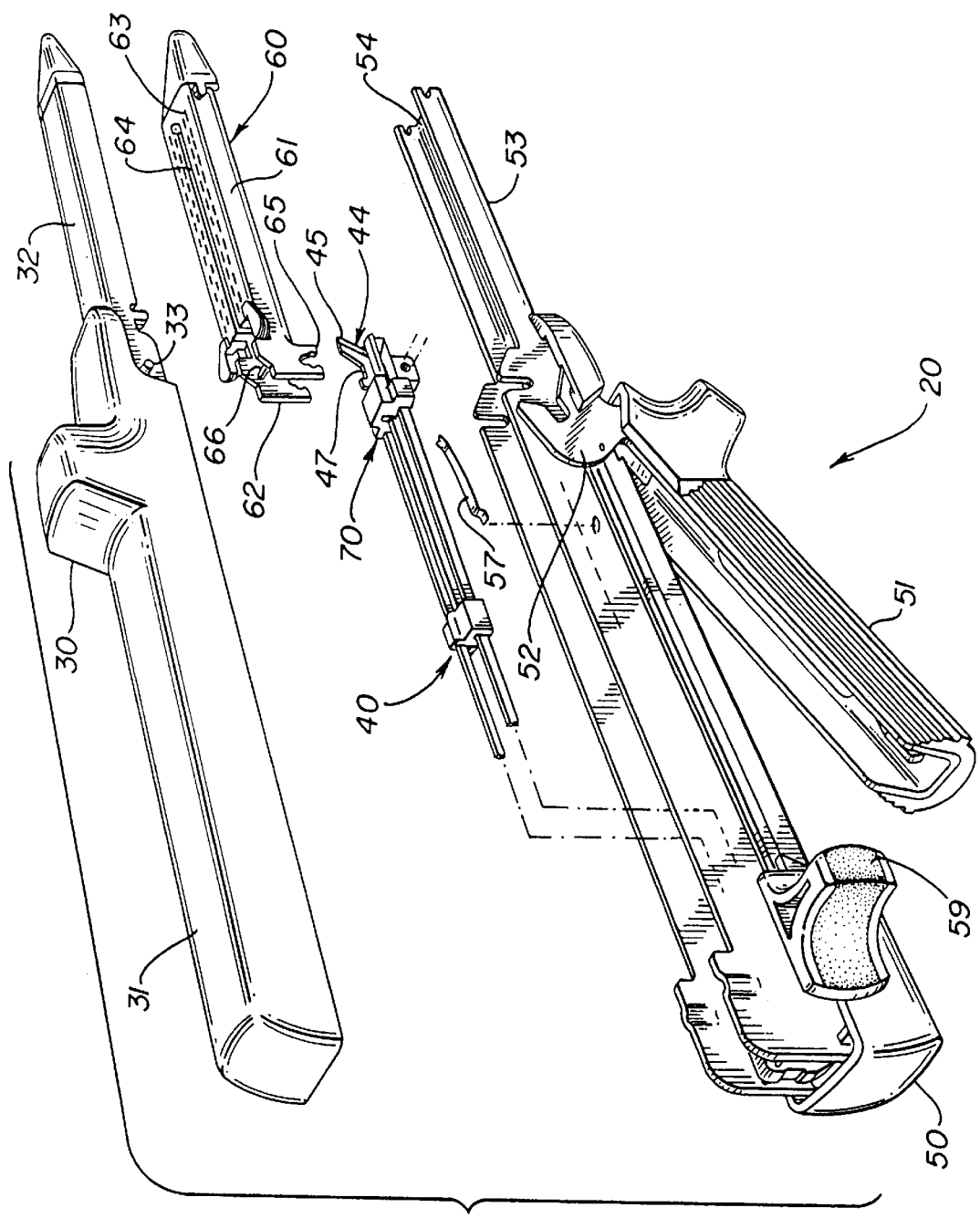
FIG. 1 is an exploded perspective view of a surgical stapler of the present invention.

As seen in FIG. 1, a typical surgical stapler 20 comprises an upper piece 30, a firing means 40, a lower piece 50 and a staple cartridge 60.

Staple cartridge 60 fits within the lower piece 50. Specifically, the front part of staple cartridge 60 fits into lower jaw channel 54. More specifically, the parallel side walls 61 of the staple cartridge 60 fit within the lower jaw channel 54. The back part of staple cartridge 60 has a breakable transverse member 66. This breakable transverse member 66 is placed on top of cartridge locking means 47 of firing means 40. At the same time two legs 65 secure staple cartridge 60 to lower piece 50. These legs 65 engage cylinder 58 of lower piece 50 in the second position, as best seen in FIG. 2.

In FIG. 1 the upper piece 30 has a rear upper handle portion 31 and a front upper jaw portion 32. Likewise, the lower piece 50 includes a rear movable lower handle portion 51 and a front lower jaw portion 53. The embodiment of the surgical stapler 20 illustrated in FIGS. 1–13 incorporates the firing means 40, leaf spring 57, and staple cartridge 60 into the lower piece 50. Yet, these elements may be placed in the upper piece 30 instead of lower piece 50.

The lower handle portion 51 illustrated in FIG. 1 is movable, more specifically, pivotable between two locking positions. In the first locking position the movable lower handle portion 51 is positioned at an oblique angle to the lower jaw portion 53. During the first locking position a C-shaped member 52 of the lower handle 51 is disengaged from a stationary locking pin 33. The upper and lower pieces, 30 and 50, respectively may be separated before or after operation of stapler 20 in the first locking position. On the other hand, in the second locking position the C-shaped member 52 of the movable lower handle 51 locks the upper and lower pieces 30 and 50 together. In the second locking position the movable lower handle portion 51 is parallel to the lower jaw portion 52. This second locking position occurs by engaging stationary locking pin 33 with C-shaped member 52. This movable handle portion design may be on the upper or lower handle portions, 31 and 51, respectively.

Figure 2:
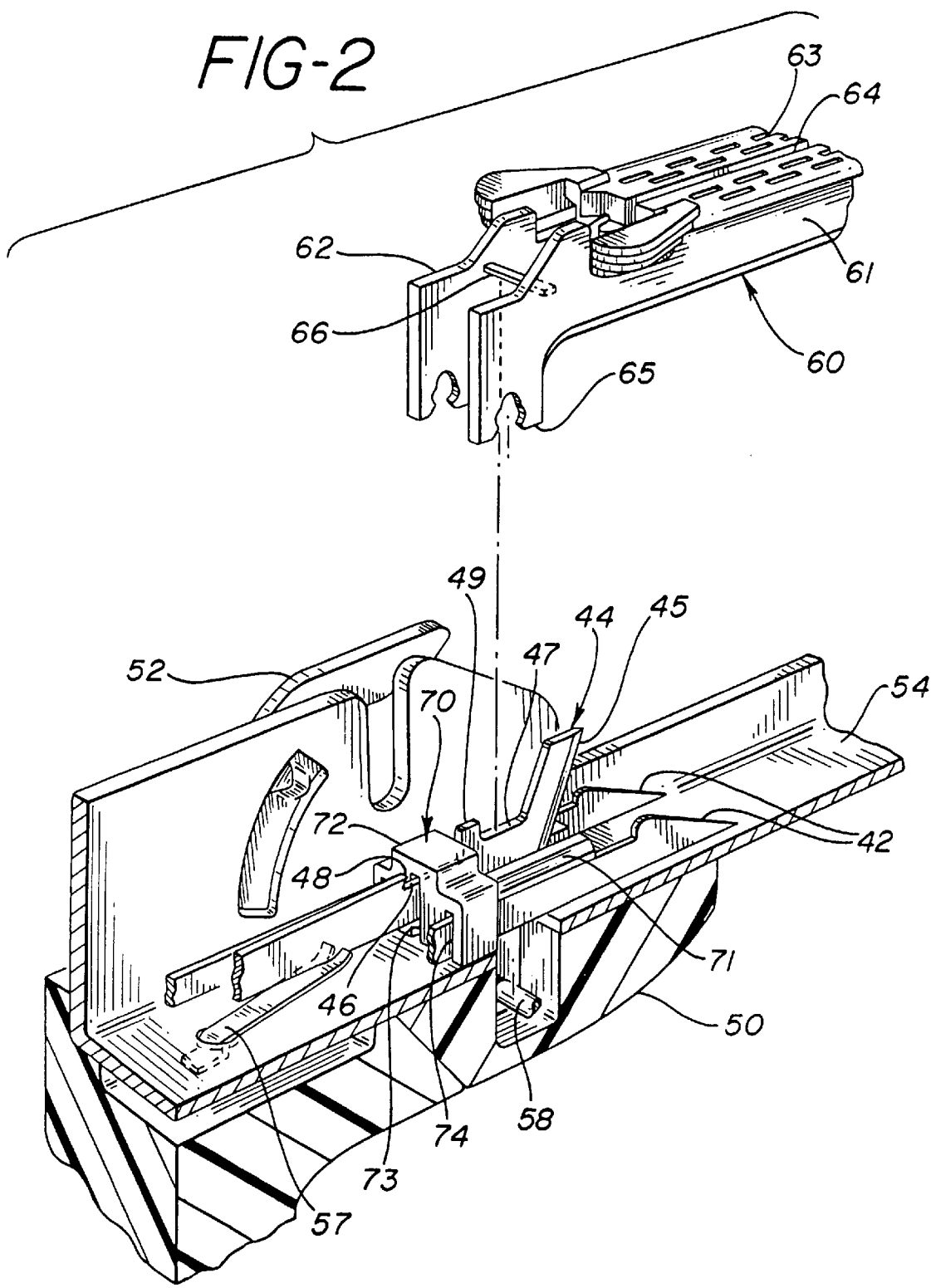
FIG. 2 is an exploded perspective view with parts of the locking mechanism broken away.

The firing means 40 will generally comprise at least one pusher bar 42, as best seen in FIG. 2. Firing knob 59 in FIG. 1 activates firing means 40 by moving pusher bars 42 through staple cartridge 60 during the second position. The firing means 40 of the present invention also includes a roof assembly 70.

The various elements of roof assembly 70 are illustrated in FIG. 2. Roof assembly 70 has a narrow roof portion 71 near the front of stapler 20. That narrow roof portion 71 is integral with a widened roof portion 72. Widened roof portion 72 has three slits. Knife slit 73 runs through both widened roof portion 72 and narrow roof portion 71. Widened roof portion 72 contains two more slits than narrow roof portion 71. The two additional slits in widened roof portion 72 are pusher bar slits 74. The width of narrow roof portion 71 is less than the transverse distance between the two pusher bars 42. So, pusher bars 42 may slide around and past narrow roof portion 71 toward the longitudinal slots 63 of staple cartridge 60. The two outer pusher bar slits 74 of the widened roof portion 72 can accommodate the two pusher bars 42. As pusher bars 42 slide through pusher bar slits 74 knife blade assembly 44 is moving forward in the second position.

Returning to FIG. 1, the firing means 40 will also contain a cutting means. Specifically, the cutting means is a knife blade assembly 44. A cutting surface 45 is included in knife blade assembly 44. Cutting surface 45 is illustrated in FIGS. 1–8. Generally, knife blade assembly 44 is placed between the pusher bars 42. Although a knife blade assembly is illustrated in FIGS. 1–13 tissue may be cut in many ways besides knife or razor blade cutting. For example, laser or chemical destruction of tissue or tearing are just a few cutting means that may be used. These and other means of cutting tissue should be considered within the scope of the present invention.

In the first position the knife blade assembly 44 is out of alignment with slot 64. In the second position knife blade assembly 44 is in alignment with slot 64. The operation of this surgical stapler 20 is similar to the operation of the surgical stapler disclosed in commonly assigned U.S. Pat. No. 4,892,244, (Fox et al.), issued Jan. 9, 1990, hereby incorporated by reference.

Figure 3:
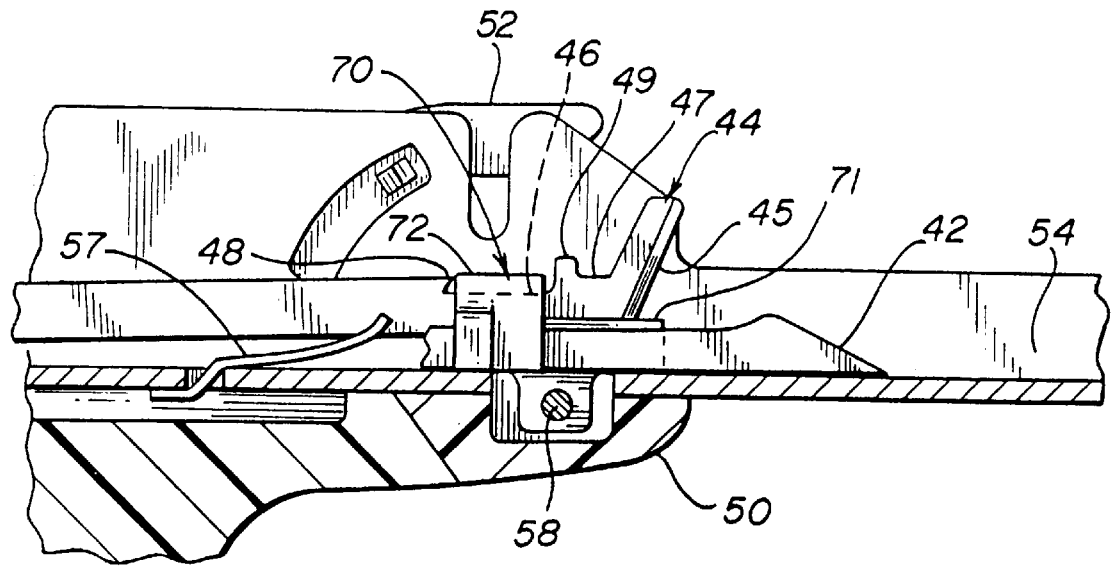
FIG. 3 is a side elevational view in partial cross-section prior to the insertion of the staple cartridge and showing the cutting means in a locked first position.
Figure 4:
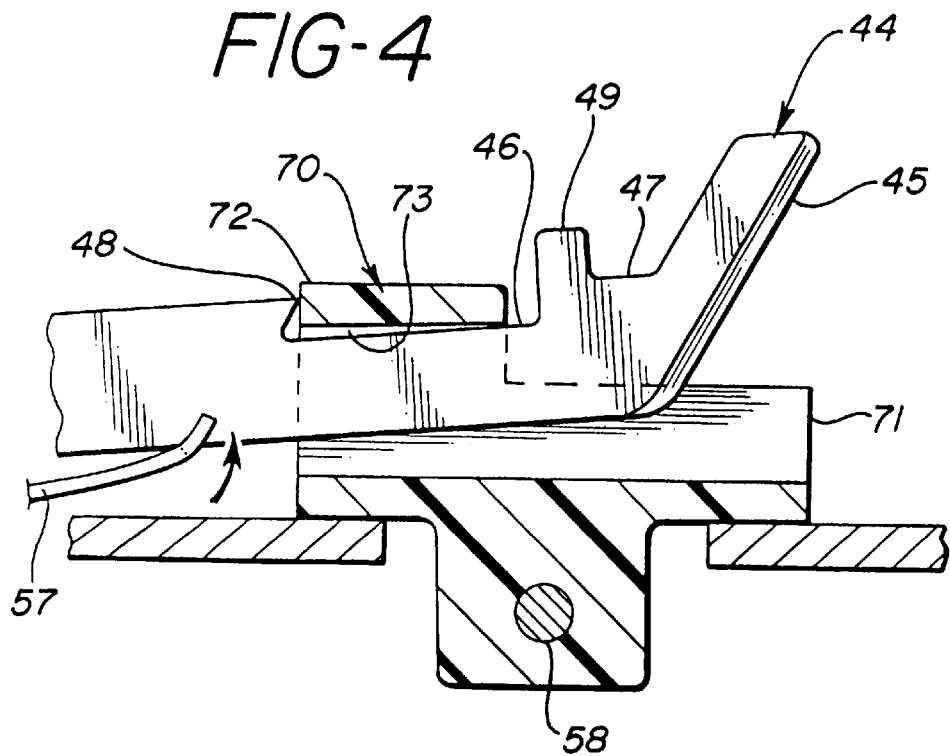
FIG. 4 is an enlarged detail view in partial cross-section showing the locking mechanism locking the cutting means in the first position.

The knife blade assembly 44 shown in FIGS. 2, 3, and 4 is locked in the first position. In the first position leaf spring 57 pushes knife blade assembly 44 up against roof assembly 70. This is best illustrated by the arrow in FIG. 4. The upward force of knife blade assembly 44 keeps widened roof portion 72 wedged in knife locking means area 46. As seen in FIGS. 3 and 4 the upward pressure of leaf spring 57 raises roof locking portion 48 to a height at which it cannot move beyond the rear of widened roof portion 72. This is true even if firing knob 59 is pushed forward in an attempt to operate stapler 20. In this first position knife blade assembly 44 cannot be moved. The two parallel pusher bars 42 cannot be moved either in the first position. Therefore, the two parallel pusher bars 42 cannot dislodge staples 80 from a full staple cartridge 60 when the knife blade assembly 44 is in the first position.

Figure 5:
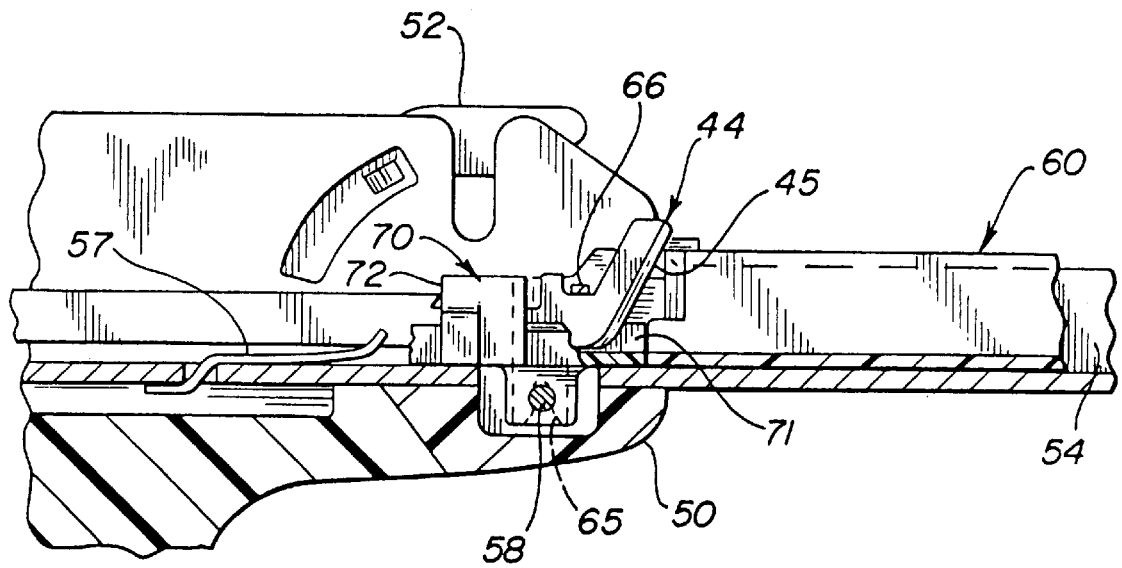
FIG. 5 is a view similar to that of FIG. 3 with a staple cartridge in place.
Figure 6:
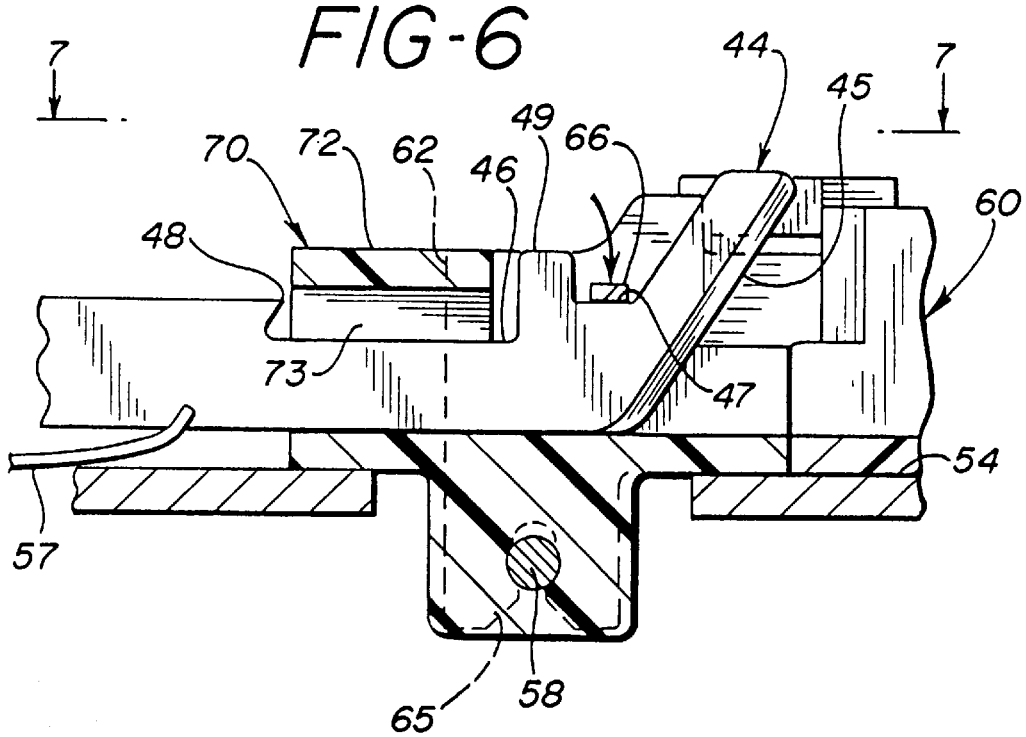
FIG. 6 is an enlarged detail view in partial cross section showing the knife blade assembly in the second position.
Figure 7:
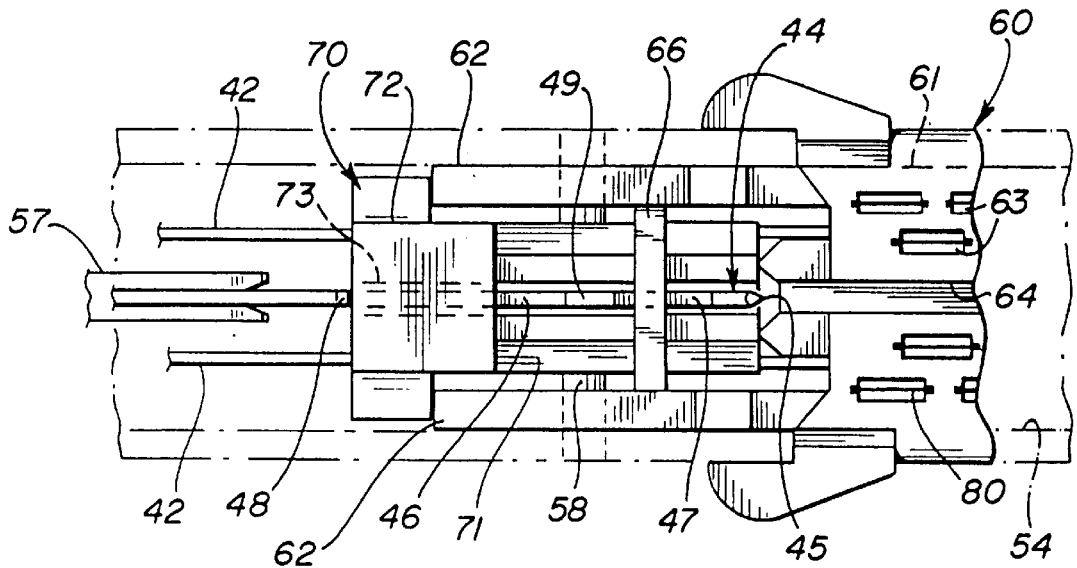
FIG. 7 is a top plan view taken along view line 7—7 of FIG. 6 showing the knife blade assembly prior to firing of the staple cartridge.

When the knife blade assembly 44 is being placed in the second position the user will hear a click as a full staple cartridge 60 is mounted. Staple cartridge 60 is mounted on lower piece 50 by engaging legs 65 of staple cartridge 60 with cylinder 58 of lower piece 50. FIG. 7 illustrates this point in time at which breakable transverse member 66 is still intact. The new staple cartridge 60 also has staples 80 in longitudinal slots 63 at this time. This same point in time is before staples 80 are fired from staple cartridge 60 and is shown in FIGS. 5 and 6. Breakable transverse member 66, seen in FIGS. 5 and 6, exerts a downward force upon cartridge locking means 47. This downward force pushes down the entire knife blade assembly 44 as well as leaf spring 57 which is below knife blade assembly 44. When this happens knife blade assembly 44 is unlocked. So, as best illustrated in FIG. 6, the user may push the firing knob 59 toward staple cartridge 60. Pushing firing knob 59 will move knife blade assembly 44 forward. When knife blade assembly 44 is unlocked the knife locking means 46 is no longer wedged under the widened roof portion 72 of roof assembly 70.

Figure 8:
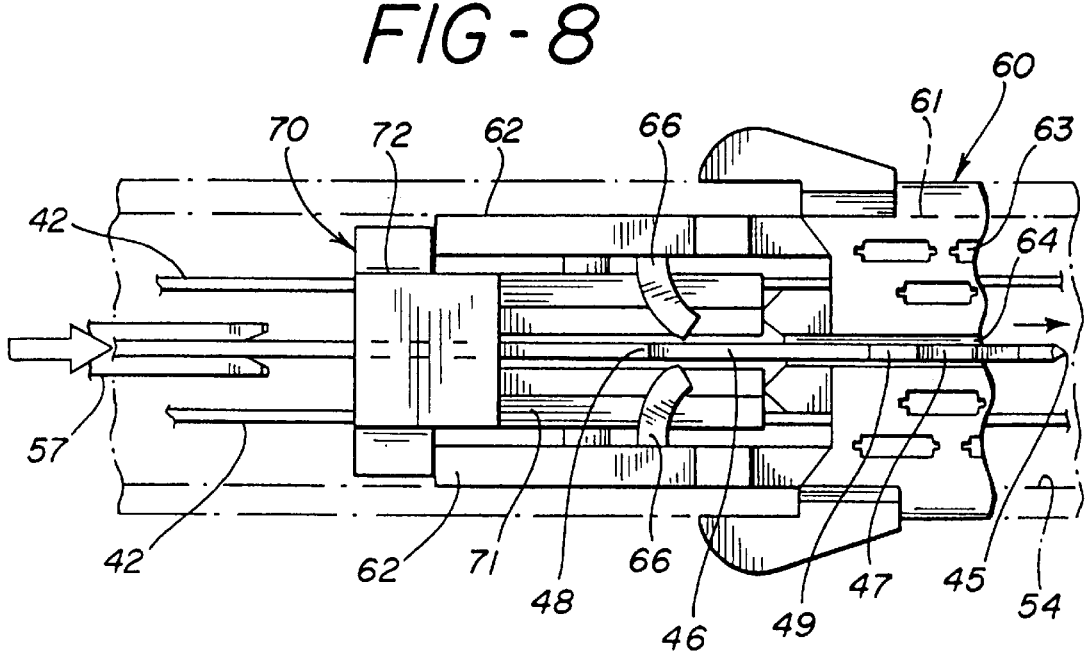
FIG. 8 is a top plan view of the assembly as shown in FIG. 7 after firing of the staples and knife blade assembly showing the broken means disposed on the cartridge of one embodiment of the invention.

Next, knife blade assembly 44 may be moved toward the staple cartridge 60. As knife blade assembly 44 is moved transverse member breaking portion 49 breaks the breakable transverse member 66. Then the knife cutting surface 45 is moved through slot 64 of staple cartridge 60. The two pusher bars 42 simultaneously remove staples 80 from staple cartridge 60. The stage after breakable transverse member 66 is broken is shown in FIG. 8. Completion of the stapling operation is illustrated by the absence of staples 80 in longitudinal slots 63. Also, breakable transverse member 66 is permanently broken so there is no way that a used staple cartridge 60' is effectively reusable.

Comparison of FIGS. 4 and 6 highlights the interaction of various parts of knife blade assembly 44 in the first position (FIG. 4) and the second position (FIG. 6). FIG. 6 is similar to FIG. 4 except that FIG. 6 includes staple cartridge 60. For example, in FIG. 6 legs 65 of staple cartridge 60 are shown in phantom. The legs 65 wrap around cylinder 58. The force exerted downward by breakable transverse member 66 is greater than the force exerted upward by leaf spring 57 in the second position. So, as a result of the force exerted by breakable transverse member 66 roof locking portion 48 has a height lower than roof assembly 70. Therefore, roof locking portion 48 no longer prohibits forward movement of knife blade assembly 44 in the second position.

Parts of the next embodiment that are the same as those of the embodiment discussed above will be referred to with the same last two digits as the corresponding parts of the previous embodiment except they will be preceded by the number 1. Another embodiment of this invention is illustrated in FIGS. 9 and 10.

Figure 9:
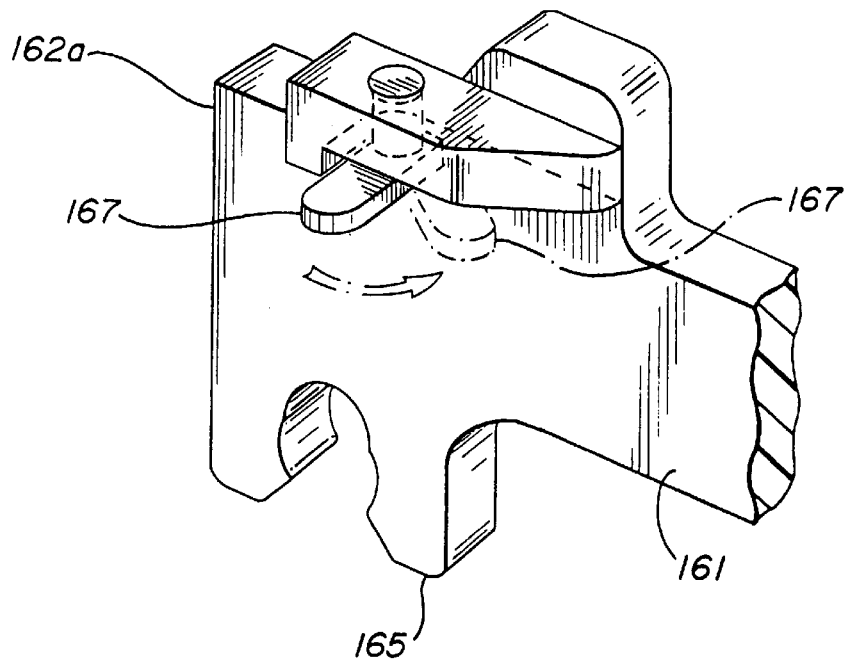
FIG. 9 is a perspective view of a locking mechanism of another embodiment of the present invention.
Figure 10:
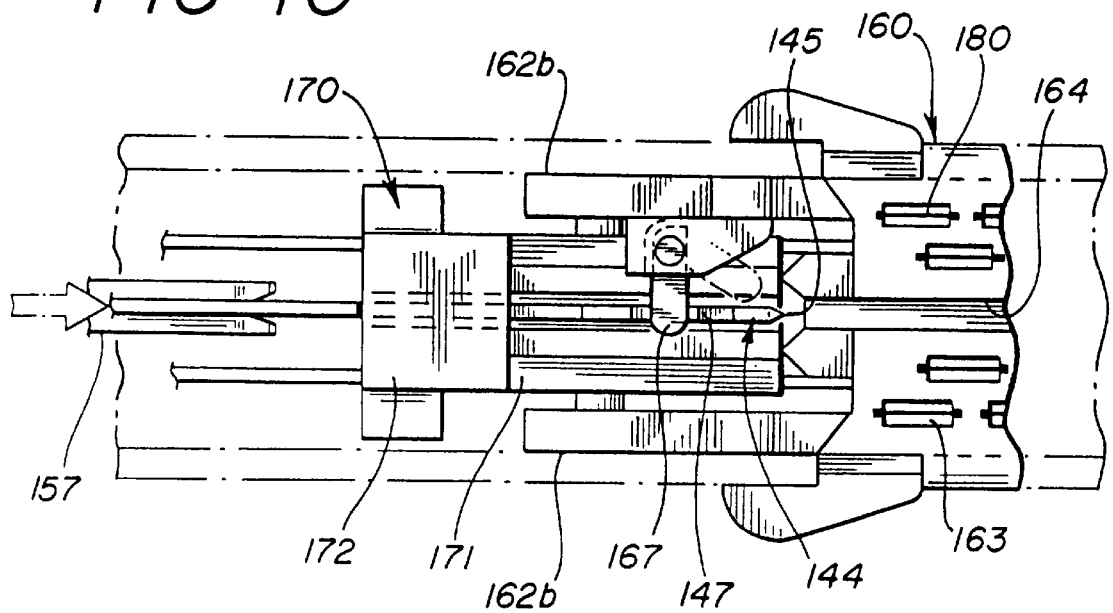
FIG. 10 is a top plan view similar to FIG. 7 showing the embodiment as depicted in FIG. 9.

The embodiment of FIGS. 9 and 10 has a rotatable member 167 that is a toggle type gate. Rotatable member 167 is affixed to a first parallel rearwardly extending surface 162a. An unused staple cartridge 160 has a rotatable member 167 that extends transversely across knife assembly 144 toward the second parallel rearwardly extending surface 162b. In the second position rotatable member 167 performs the same function as breakable transverse member 66 by depressing knife blade assembly 144. The rotatable member 167 is shown in the second position engaging cartridge locking means 147. When the rotatable member engages cartridge locking means 147 it depresses leaf spring 157. After leaf spring 157 is depressed knife blade assembly 144 may be moved toward staple cartridge 160.

The arrow in FIG. 9 shows how rotatable member 167 is rotated to the side when knife blade assembly 144 is moved forward toward staple cartridge 160. Rotatable member 167 is parallel to knife blade assembly 144 in the first position. This is shown in phantom in FIGS. 9 and 10.

Figure 11:
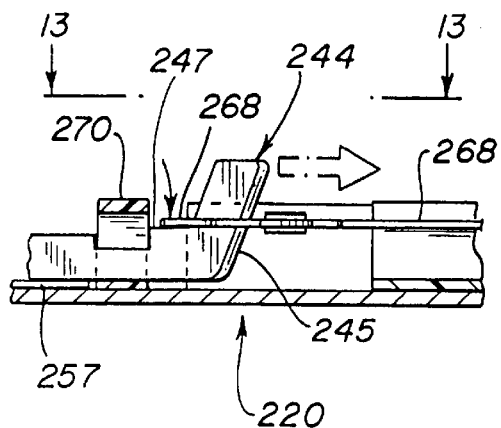
FIG. 11 is a schematic side elevational view showing yet another embodiment of a locking mechanism of the present invention in partial cross-section when the knife blade assembly is moving forward through the cartridge slot of a staple cartridge containing staples.
Figure 12:
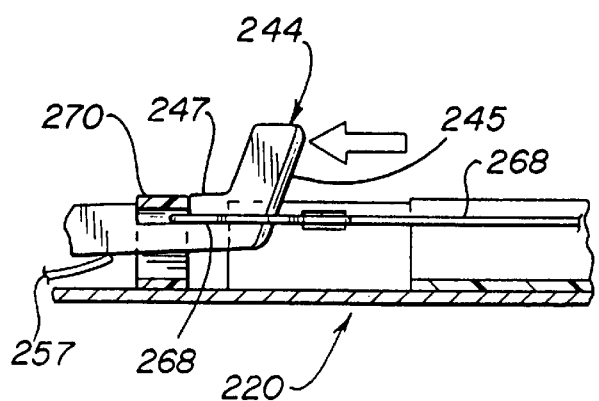
FIG. 12 is a schematic side elevational view showing the embodiment depicted in FIG. 11 in partial cross-section when the knife blade assembly is moving backward through the cartridge slot of a staple cartridge that no longer contains staples.
Figure 13:
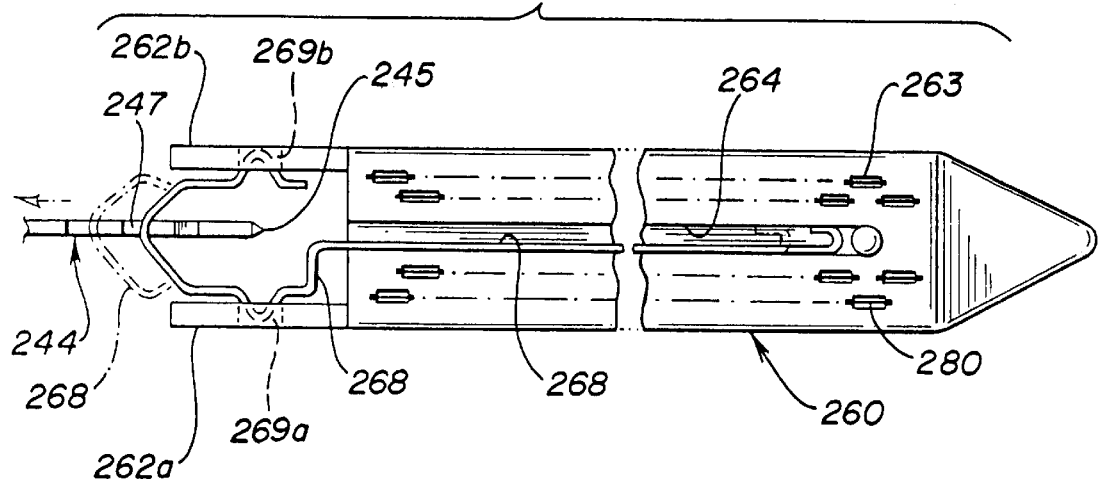
FIG. 13 is a top plan view similar to FIG. 10 showing the embodiment depicted in FIG. 11.

Parts of the next embodiment that are the same as those of the first embodiment discussed above will be referred to with the same last two digits as the corresponding parts of the first embodiment discussed except they will be preceded by the number 2. Yet another embodiment of this invention is illustrated in FIGS. 11, 12 and 13 which requires that a configured wire member 268 be in staple cartridge 260. This embodiment also requires that two cavities 269a and 269b be molded into the two parallel rearwardly extending surfaces 262a and 262b.

FIG. 13 shows that the configured wire member 268 extends along substantially the entire length of cartridge slot 264 into the first cavity 269a. Then the configured wire member 268 extends along the first parallel rearwardly extending surface 262a. Next, configured wire member 268 extends across the top surface of cartridge locking means 247. After that, configured wire member 268 extends along the second parallel rearwardly extending surface 262b. Finally, the configured wire member 268 extends into and out of the second cavity 269b to its termination along the front of the second parallel rearwardly extending surface 262b.

FIG. 11 illustrates this embodiment in the second position. In FIG. 11 configured wire member 268 engages the top surface of knife blade assembly 244. Configured wire member 268 does this at cartridge locking means 247. The arrow in FIG. 11 indicates that knife blade assembly 244 can move forward. Knife blade assembly 244 can move forward because configured wire member 248 is pressing down knife blade assembly 244. The comparison of FIGS. 4 and 6 with respect to the first embodiment described applies to a comparison of FIGS. 11 and 12 of the embodiment just described.

FIG. 12 illustrates configured wire member 268 in the first position when it cannot hold down the top surface of cartridge locking means 247. The configured wire member 268' shown in phantom in FIG. 13 is released from the cavities 269a and 269b. As a result, it does not exert sufficient downward force upon knife blade assembly 244 to counteract the upward force of leaf spring 257. Therefore, it is necessary to place a fresh staple cartridge 260 in the stapler 220. That is, if the operator desires to return the stapler 220 to the second position in which the knife blade assembly 244 is movable.

The unique combination of features possessed by the present invention render them well suited for use within a surgical stapler, in order to prevent refiring or reloading of a spent surgical staple cartridge. This enhances speed and time of performance for the surgeon. Naturally, these combinations may be useful for other types of cartridge-loading mechanisms. Of course, while several means are available, the particular advantageous embodiments have been chosen to illustrate the invention. It will be understood by those skilled in the art that various changes and modifications may be made in the invention without departing from its scope, which is defined by the following claims and their equivalents.

What is claimed is:

1. A surgical stapler comprising:
   a cartridge having a plurality of rows of staples disposed along a longitudinal axis of said cartridge;
   at least one pusher bar movable distally within said cartridge for ejecting said staples;

a lockout member movable distally in said stapler, said lockout member being further movable generally perpendicularly to the direction of distal movement of said lockout member; and a barrier engageable by said lockout member in a retracted position of said lockout member, subsequent to an initial distal movement of said lockout member.

2. A surgical stapler in accordance with claim 1, wherein said lockout member comprises an elongated member having a notched surface.

3. The stapler of claim 1 wherein said barrier comprises a first surface extending generally transversely to said longitudinal axis for engagement by said lockout member.

4. A surgical stapler in accordance with claim 1, further comprising a knife.

5. A surgical stapler in accordance with claim 1 wherein said lockout member comprises a knife blade.

6. A surgical stapler in accordance with claim 1 further including a stop member comprising a roof assembly.

7. A surgical stapler in accordance with claim 1, wherein said lockout member is spring biased generally perpendicularly to the direction of distal movement thereof toward a position for engaging said barrier.

8. A surgical stapler in accordance with claim 7, wherein said lockout member is biased by a leaf spring.

9. A surgical stapler in accordance with claim 1, further comprising a movable restraint on said stapler engaged with said lockout member during a portion of the distal movement of said lockout member.

10. A surgical stapler in accordance with claim 9, wherein said restraint comprises a rotatable member.

11. A surgical stapler in accordance with claim 9, wherein said lockout member is spring biased generally perpendicularly to the direction of distal movement thereof toward a position for engaging said barrier, said restraint acting to prevent engagement of said lockout member with said barrier prior to at least a portion of a distal movement of said lockout member.

12. A surgical stapler comprising:

a frame means and a cartridge having a plurality of rows of staples defining a longitudinal axis of said stapler; firing means movable relative to said frame means to fire the staples along said axis; and a lockout mechanism for preventing a subsequent longitudinal firing movement of the firing means after at least a portion of said firing means has been moved to a retracted longitudinal position opposite to a direction of firing movement of said firing means, said lockout mechanism comprising a lockout member movable distally within said stapler and movable generally perpendicular to the direction of distal movement from a first position to a second position, a restraint for maintaining said lockout member in said first position thereof during at least a portion of a distal movement of said lockout member so that said firing means fires said staples, said restraint being movable in response to firing movement of said firing means so that said lockout member is moved to said second position to prevent refiring after at least a portion of said firing means moves to said retracted position.

13. A surgical stapler of claim 12 further comprising a knife blade.

14. A surgical stapler in accordance with claim 12, wherein said restraint comprises a member movably mounted on said stapler.

15. A surgical stapler in accordance with claim 14, wherein said movably mounted member is rotatable.

16. A surgical stapler in accordance with claim 12, wherein said lockout member comprises a notched surface engageable with a barrier for preventing subsequent longitudinal movement of said firing means.

17. A surgical stapler in accordance with claim 16, wherein said lockout member is located on said knife blade.

18. A surgical stapler comprising:

a cartridge having a plurality of rows of staples disposed along a longitudinal axis of said cartridge;

at least one pusher bar movable distally within said cartridge for ejecting said staples;

a lockout member movable distally in said stapler, said lockout member being further movable generally perpendicularly to the direction of distal movement of said lockout member; and a barrier member engageable by said lockout member in a retracted position of said lockout member, subsequent to an initial distal movement of said lockout member; and wherein said lockout member is spring biased generally perpendicularly to the direction of distal movement thereof toward a position for engaging said barrier, said restraint acting to prevent engagement of said lockout member with said barrier prior to at least a portion of a distal movement of said lockout member.

19. A surgical stapler for applying a plurality of rows of staples, said rows of staples being housed in a disposable cartridge having a front portion and a rear portion, said cartridge having a cartridge slot disposed between adjacent rows of staples and extending substantially the entire length of said rows, said stapler including firing means for said staples, cutting means movable in said slot and a locking mechanism for preventing movement of said cutting means in said slot, said cutting means having a bottom surface, a top surface, and a cutting edge, said locking mechanism comprising a leaf spring disposed in said stapler and engaging the bottom surface of said cutting means, to place said cutting means in a first position out of alignment with said slot, means disposed on said cartridge for engaging the top surface of the cutting means to depress said leaf spring and move said cutting means from said first position to a second position in alignment with said slot whereby said cutting means may move within said slot.

* * * * *